(12) United States Patent
Kuebler et al.

(10) Patent No.: US 8,303,553 B2
(45) Date of Patent: Nov. 6, 2012

(54) FLOW LIMITER FOR A FLUID FLOWING IN AN ASPIRATION BRANCH OF A SURGICAL SYSTEM, AND SURGICAL SYSTEM

(75) Inventors: Christoph Kuebler, Oberkochen (DE); Martin Kraus, Huettlingen (DE); Michael Eichler, Aalen (DE); Tobias Maier, Stuttgart (DE)

(73) Assignee: Carl Zeiss Meditec AG, Jena (DE)

( * ) Notice: Subject to any disclaimer, the term of this patent is extended or adjusted under 35 U.S.C. 154(b) by 302 days.

(21) Appl. No.: 12/666,059

(22) PCT Filed: Jun. 19, 2008

(86) PCT No.: PCT/EP2008/057823
§ 371 (c)(1),
(2), (4) Date: Apr. 13, 2010

(87) PCT Pub. No.: WO2009/007223
PCT Pub. Date: Jan. 15, 2009

(65) Prior Publication Data
US 2010/0305496 A1 Dec. 2, 2010

(30) Foreign Application Priority Data
Jul. 6, 2007 (DE) .......................... 10 2007 031 618

(51) Int. Cl.
*A61B 17/32* (2006.01)

(52) U.S. Cl. ........... 604/317; 604/118; 604/319; 604/22
(58) Field of Classification Search .................. 604/31, 604/35, 22, 107, 18, 277, 317, 319; 600/565; 607/107
See application file for complete search history.

(56) References Cited

U.S. PATENT DOCUMENTS

| | | |
|---|---|---|
| 6,398,754 B1 | 6/2002 | Sutton et al. |
| 2002/0022810 A1* | 2/2002 | Urich ............................ 604/317 |
| 2003/0236508 A1 | 12/2003 | Cull |
| 2004/0039351 A1* | 2/2004 | Barrett ........................... 604/272 |
| 2005/0113741 A1* | 5/2005 | Huang et al. .................... 604/35 |
| 2006/0224163 A1 | 10/2006 | Sutton |

FOREIGN PATENT DOCUMENTS
WO WO 02/19896 3/2002

* cited by examiner

*Primary Examiner* — Laura Bouchelle
(74) *Attorney, Agent, or Firm* — Fish & Richardson P.C.

(57) ABSTRACT

The invention relates to a flow limiter for a fluid flowing in an aspiration branch of a surgical system, which fluid is a surgical fluid and has emulsified particles in a surgical intervention, with a limiter element that comprises at least one flow channel arrangement with at least one main channel and at least one subsidiary channel that opens into the main channel at an angle of greater than or equal to 90°. The invention also relates to a surgical system, in particular an ophthalmic microsurgical system for lens surgery.

20 Claims, 7 Drawing Sheets

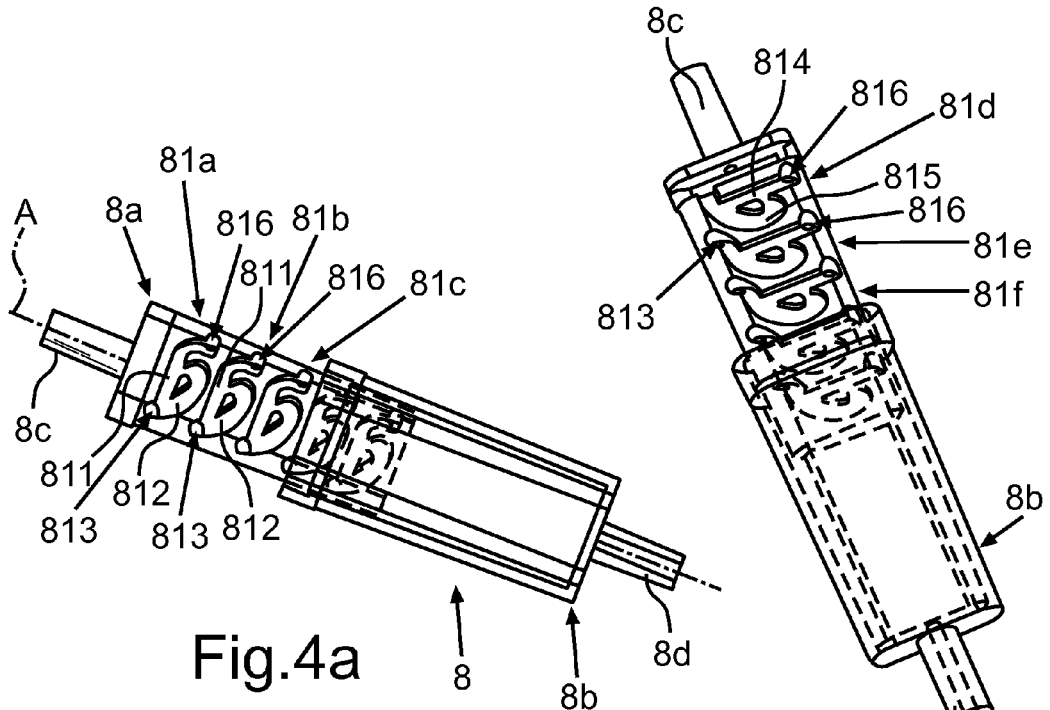
Fig.4a
Fig.4b
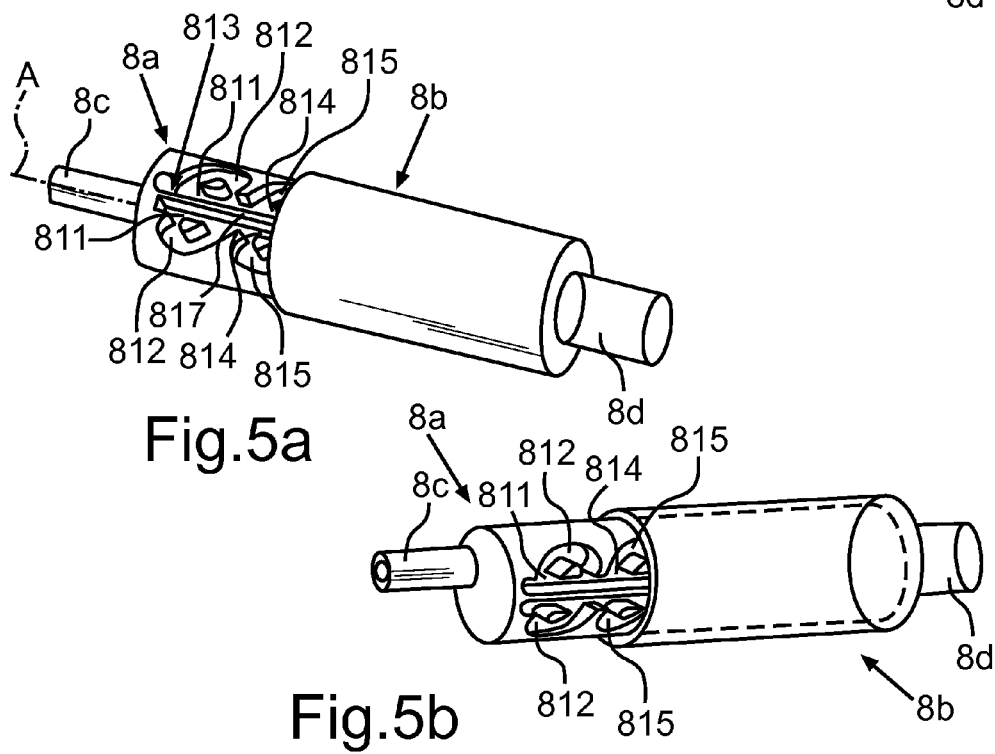
Fig.5a
Fig.5b

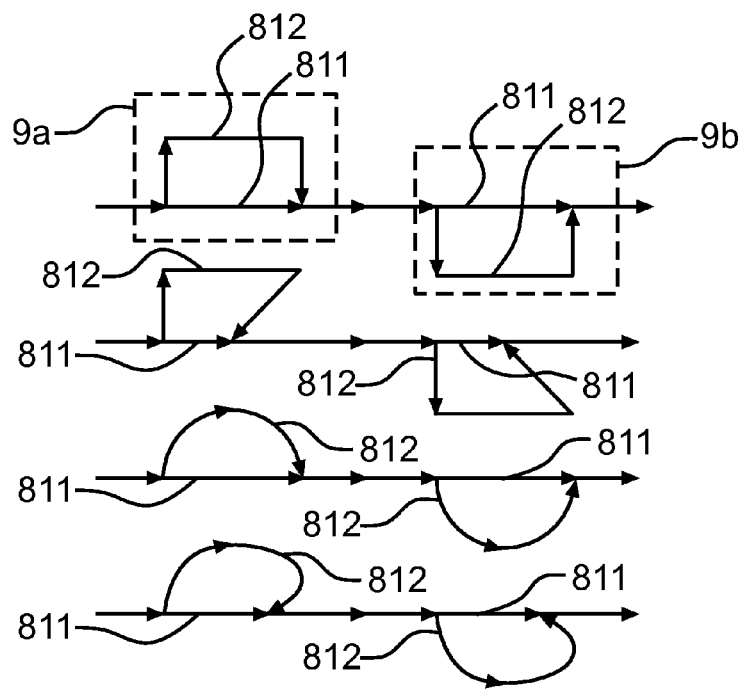
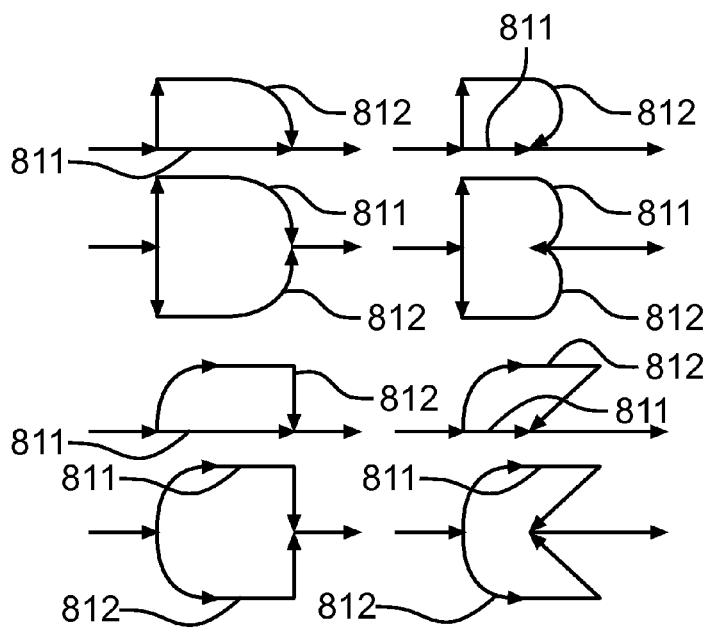

FLOW LIMITER FOR A FLUID FLOWING IN AN ASPIRATION BRANCH OF A SURGICAL SYSTEM, AND SURGICAL SYSTEM

CROSS-REFERENCE TO RELATED APPLICATIONS

This application is the National Stage of International Application No. PCT/EP2008/057823, filed Jun. 19, 2008, which claims the benefit of German Application No. 10 2007 031 618.8, filed Jul. 6, 2007. International Application No. PCT/ EP2008/057823 is incorporated by reference herein in its entirety.

TECHNICAL FIELD

The invention relates to a flow limiter for a fluid flowing in an aspiration branch, and to a surgical system, in particular an ophthalmological microsurgical system for lens surgery.

PRIOR ART

Phacoemulsification is a very frequently used technique in ophthalmology in which a surgical handpiece is used as a microsurgical tool. This handpiece generally comprises a tip in the form of a hollow needle with a relatively small diameter which can be designed for emulsifying, fragmenting and/or cutting tissue after said tip has been inserted into an incision in the cornea or sclera of the eye. Additionally, this tip of the handpiece can have a central channel which is connected to a suction source, for example a pump, which suctions off the tissue remains of the fragmented lens from the eye. Furthermore, the handpiece can be designed for supplying a rinsing fluid, for example a saline solution (BSS solution), to the eye for the purposes of rinsing the eye during the treatment. The removed tissue which is suctioned off from the eye together with the rinsing fluid is for example collected in a collection container which is usually arranged at a distance from the handpiece. The handpiece typically comprises an ultrasound apparatus for fragmenting the lens of the eye, which ultrasound apparatus excites the tip of the eye to oscillate. This oscillation of the tip fragments the lens into small parts.

A surgical system generally also comprises a user interface designed for communication with microsurgical instruments.

The fluidics system in a phacoemulsification system is subdivided into two functional groups. The irrigation system waters the eye using a rinsing fluid during the operation. At the same time, a pump aspiration system suctions off the lens material that was emulsified as a result of the ultrasound process. These two functions of the fluidics module are connected to the phaco-handpiece by means of a flexible tube system. During the phase of operation, the rinsing fluid supply is controlled in the irrigation branch by an irrigation valve. The suction pressure is measured in the aspiration branch during the suctioning off and is used for monitoring and controlling the fluidics and ultrasound systems.

In said surgical systems, the pressure in the fluid can vary during operation of the components. This can occur in particular in the aspiration branch, as a result of which the suctioning off can only be effected in a suboptimal fashion and the surgical procedure can be adversely affected.

The narrowest point, and hence the minimum internal diameter, of the phaco-handpiece of the surgical equipment through which the fragmented and emulsified cataract material must be suctioned off is found in the aspiration branch, particularly at the tip of the hollow needle. It is possible that this tip of the hollow needle becomes blocked during the suctioning off of the lens remains in the surgical intervention. In the case of such a blockage, the medical practitioner must increase the suction pressure on the aspiration side until the particle is suctioned through the narrow region of the handpiece tip. At the moment of the breakthrough in particular, at which the blocking particle can be suctioned through, a large volume is briefly suctioned out of the eye and so the intraocular pressure decreases relatively strongly. This brief pressure pulse when this blocking particle breaks through can damage important elements of the eye, in particular in the posterior capsular bag, and therefore the overall success of the cataract operation can be adversely affected.

U.S. Pat. No. 6,398,754 B1 discloses a method in which a bypass bore is produced between the irrigation branch and the aspiration branch in the vicinity of the tip of the hollow needle of the handpiece. A significant disadvantage thereof can be seen in the fact that the bypass connection between irrigation and aspiration only permits a relatively low suction pressure to be formed, and the latter is significantly smaller than in a design without such a bypass bore. This significantly adversely affects the basic functionality of the entire system. Moreover, as a result of the bypass bore, a liquid volume is still additionally extracted briefly via two lines from the eye in the case of a particle breakthrough and so the pressure pulse generated by the breakthrough effects a significant drop in pressure in the eye.

US 2004/0039351 Al discloses a flow limiter in which an attempt is made to generate turbulent flow by a line section in the aspiration line and an attempt is made to limit the flow. To this end, grooves and recesses are formed on the inner side of the tube-shaped flow limiter. As a result, the cross section of the channel has outwardly arched dents. Only a relatively small pressure loss can be attained as a result of these modifications of the cross section, particularly in the case of relatively small Reynolds numbers. This is because every recess increases the cross section of the channel segment and thus decreases the turbulent resistance.

DESCRIPTION OF THE INVENTION

It is an object of the present invention to develop a flow limiter for an aspiration device, and a surgical system, in which the pressure pulse or pressure oscillations occurring as a result of a particle breakthrough in the aspiration device can be limited or reduced.

This object is achieved by a flow limiter and a surgical system in accordance with the independent claims.

A flow limiter according to the invention is designed to limit the flow of a fluid flowing in an aspiration branch of a surgical system. The fluid is a surgical fluid and has emulsified particles during a surgical intervention. The flow limiter comprises a limiter element which has at least one flow channel arrangement with at least one main channel and at least one secondary channel. The secondary channel opens into the main channel at an angle of 90° or more. As a result, a pressure pulse or a pressure oscillation can be at least significantly reduced in that specific operational state in which there is a particle breakthrough in the aspiration device. Hence, the flow limiter according to the invention permits the development of a fluidic resistance element which in the mentioned specific operational states can effectively limit pressure pulses in an aspiration device, particularly in an aspiration branch in which a fluid flows. This can also prevent states which can be generated by such a pressure pulse or such a pressure oscillation as a result of a particle breakthrough in the aspiration branch.

The flow limiter, and particularly the limiter element with the flow channel arrangement, is preferably designed such that a turbulent flow of the fluid can be generated in the flow limiter as a function of a specific operational state of the aspiration device, particularly of the surgical system comprising the aspiration device.

Both channels of the flow channel arrangement are provided for aspirative fluid transport, in particular for simultaneous aspirative fluid transport.

The flow limiter, and particularly the flow channel arrangement of a limiter element, is preferably designed such that a turbulent flow can be generated at a Reynolds number of less than 2000. If the prescribed system dimensions are taken into account, it is relatively difficult to be able to generate sufficiently turbulent flows, particularly in this range of the Reynolds number, in order to be able to effectively limit such pressure pulses or pressure oscillations in the case of particle breakthroughs. However, this can be attained by the flow limiter according to the invention.

The flow limiter is preferably designed such that a pressure loss coefficient $\zeta$ per limiter element of the flow limiter is greater than or equal to 6, in particular greater than or equal to 8, in particular greater than or equal to 12. The flow limiter preferably has an overall design such that a pressure loss coefficient $\zeta$ has a value of greater than 70, in particular 85. Provision can preferably be made for a plurality of limiter elements to be combined in order to be able to obtain this pressure loss coefficient for the entire flow limiter. Nevertheless, an installation-space minimized and compact arrangement can also be afforded as a result of the structural design of the limiter element of a flow limiter with a plurality of such limiter elements. This structural design also affords the possibility of creating such a high value of a pressure loss coefficient $\zeta$ for the overall arrangement of the flow limiter with relatively small dimensions.

A limiter element preferably has an integral design. A flow channel arrangement in a limiter element can be completely embedded in said limiter element. As a result of this, all channel walls along the length of the channels are formed by the material of the limiter element.

When viewed along its length, provision can also be made for a flow channel arrangement to be arranged in the limiter element such that it is at least in part uncovered toward the outside. In the case of such an embodiment, provision can then be made for an additional cover which is preferably designed in the shape of a plate and used to close the channels. The cover can be detachably affixed to the limiter element.

In the case of a plurality of limiter elements, provision can be made for an external wall of a limiter element to be used as a cover for the partly open flow channels formed in the other limiter element and provision can be made for a corresponding sealing attachment.

The outlet of one limiter element then opens into the inlet of the other limiter element.

The secondary channel is preferably arranged outside of the main channel and the turbulent flow can be generated in the flow direction of the fluid at the confluence of the secondary channel into the main channel. Thus, provision is not made for an embodiment where one channel is guided within the other, but, when viewed in the longitudinal direction, the channels are spaced apart and separated from one another. The confluent contact between the channels is only produced at the ends. Each channel thus is delimited, as it were, by its own walls on its shell.

The secondary channel arranged outside of the main channel preferably opens into the main channel with both its ends. As a result of this there is, as it were, a parallel connection of the flow channels and a particularly effective flow limitation is obtained in the case of particle breakthroughs.

The flow limiter preferably comprises a region through which fluid flows, particularly in the flow channel arrangement, which region has a minimum internal dimension which is greater than the minimum internal dimension of a hollow needle of a surgical handpiece which can be connected to the flow limiter in the aspiration branch. This can prevent a particle to be suctioned off from becoming stuck in the flow limiter and generating a further blockage. The cross section of the region of the flow limiter through which fluid flows can have a round, oval or any other design without corners. However, provision can likewise be made for a cross-sectional shape with corners. The internal dimension is understood to be the straight-lined connection between two points on the cross-sectional border of the region of the flow limiter through which fluid flows, which line passes through the center point or center of gravity of the geometrical cross-sectional shape.

In particular, provision is made for the minimum internal dimension of the region through which fluid flows to be at least 10%, in particular at least 20%, in particular at least 30%, in particular at least 40% and in particular 50% greater than the minimum internal dimension of the hollow needle.

It was found to be particularly preferable if the minimum internal diameter of the hollow needle is less than 1 mm, in particular 0.8 mm. The minimum internal dimension of the region of the flow limiter through which fluid flows preferably has a value of between 1.1 mm and 1.6 mm, in particular of between 1.2 mm and 1.4 mm.

The flow limiter is preferably designed such that the flow rate is greater than or equal to 190 ml per minute, in particular approximately 200 ml per minute. Such through-flow quantities are substantially greater than are found in micro-systems technology, for example. As a result of this there are also fundamentally different flow-technical conditions. Furthermore, ultrapure liquids are used in micro-systems technology; this is not the case in the present flow limiter comprising the particle-contaminated surgical fluid.

The flow limiter is preferably arranged in the aspiration branch, as close as possible to the handpiece. In particular, provision can be made for the flow limiter to be arranged directly on the handpiece. Provision can likewise be made for the flow limiter to at least in part be arranged in the handpiece. The closer the flow limiter is arranged on the handpiece and, in particular, the closer it is arranged to the tip of the hollow needle of the handpiece, the more effectively the pressure pulse or the pressure oscillation can be prevented in the case of a particle breakthrough.

The internal dimension of the region of the flow limiter through which fluid flows, in particular the flow channel arrangement on a limiter element, preferably remains substantially unchanged over the entire length. However, provision can also be made for the internal dimension of this region of the flow limiter through which fluid flows to change at least once over the entire length.

Provision can be made for the inner side of the region of the flow limiter through which fluid flows to be at least in part elastic to force actions on the inner side generated by fluid flows. However, provision can likewise be made for the entire length of this inner side to be stiff to force actions as generated by pressure-pulsed fluid flows.

The main channel and the secondary channel are preferably designed and arranged such that the turbulent flow, when viewed in the direction of the flow, can be generated in the region of the confluence of the secondary channel into the main channel.

A flow limiter preferably comprises at least two limiter elements, which can be connected to and separated from one another nondestructively and in a reversibly detachable fashion. Therefore, the limiter elements are individual parts which can be joined. This affords the possibility of individually carrying out a simple exchange or a composition of a flow limiter with an arbitrary number of limiter elements. A modular design of the flow limiter affords high compatibility when used in different systems and ensures a quick and uncomplicated installation.

Provision can also be made for at least two limiter elements of a flow limiter to be interconnected not in a nondestructive detachable fashion but to be fixedly interconnected. Such an integral design affords optimum guidance of the flow channel arrangement and can avoid tolerance inaccuracies which may occur in the case of detachably interconnected limiter elements.

The at least two limiter elements are preferably in a stacked arrangement and so installation space can be minimized. In particular, the limiter elements are arranged on top of one another like a tower.

Every limiter element preferably has at least two flow channel arrangements. This design can be more effective at limiting a pressure pulse or a pressure oscillation in the case of a particle breakthrough in the aspiration device or in the aspiration branch and moreover a compact and confined design of the flow limiter can be obtained.

Provision can be made for the at least two flow channel arrangements to be formed on opposite sides of the limiter element when viewed in the longitudinal direction of the flow limiter and for said flow channel arrangements to be interconnected via channel connections. Provision can preferably be made for a plurality of limiter elements to be connected, as it were, in series when viewed in the longitudinal direction of a flow limiter, and for every limiter element to comprise at least two flow channel arrangements which are arranged on opposite sides in a length section of the flow limiter. Hence, in each case one flow channel arrangement is formed on opposite sides of a same length section of the flow limiter.

The limiter elements of a flow limiter, and in particular the flow channel arrangements of the limiter elements, can preferably be arranged in a cascading or step-like fashion when viewed in the longitudinal direction of the flow limiter. A flow channel arrangement arranged on one side of the flow limiter then opens into a flow channel arrangement arranged on the other side of the flow limiter, the latter flow channel arrangement being formed such that it is offset in the longitudinal direction in relation to said other side. The effectiveness of limiting a pressure pulse or a pressure oscillation in the case of a particle breakthrough in the aspiration branch can thus again be significantly improved and the structure can be minimized.

Provision can preferably be made for the main channel and the secondary channel of a flow channel arrangement to be arranged in a plane which is vertical to the inlet and/or the outlet of the aspiration line of the aspiration branch into the flow limiter. This arrangement affords the possibility of forming as many of such flow channel arrangements as possible in a relatively small space. As a result of the flow channel arrangement extending perpendicularly to the longitudinal direction, the flow limiter is virtually minimized in terms of its external design length but it nevertheless permits main channels and secondary channels of long lengths.

Particularly when the flow limiter is arranged directly on, or even partly in the handpiece, one or more of the above-mentioned advantageous embodiments can permit the development of a very short arrangement with very efficient flow limiting, the arrangement of handpiece and flow limiter nevertheless being very handy. The flexible operation and simple mobility of this arrangement can be ensured, particularly when an aspiration line is also connected.

A flow limiter preferably comprises a rod-shaped internal part with flow channel arrangements and a separate external part which can be slid onto the internal part and which external part covers the flow channel arrangements in the state where it is joined to the internal part. The flow channel arrangements are preferably formed in the shell of the internal part and hence are, as it were, designed as flow channels which are open toward the outside. The external part preferably has an accurately fitting design and, when the internal part is attached to or slid into the hollow external part, the inner wall of the external part forms a sealing cover for the open flow channel arrangements in the internal part. In the case of such a design, the flow limiter is realized as a simple plug connection or coupling. In addition to a simple and quick installation, the flow channel arrangements can also be cleaned in an uncomplicated and rapid fashion because the flow channel arrangements are uncovered over virtually their entire length and are visible when the internal part is pulled out of the external part. Hence said flow channel arrangements are also accessible in a relatively simple fashion.

Flow channel arrangements are preferably formed on both sides of the rod-shaped internal part. These opposing flow channel arrangements can in each case be connected in pairs by a channel connection. However, provision can also be made for in each case a plurality of flow channel arrangements to be formed on both sides of the internal part, when viewed in the longitudinal direction, and for respectively only those flow channel arrangements which are arranged on one side of the internal part to be interconnected over the entire length. It is only at the end of the length of the flow limiter that a channel connection is established to the flow channel arrangements arranged on the opposite side of the internal part.

When viewed in the longitudinal direction, provision can likewise be made for the flowing fluid in each case to be guided from a flow channel arrangement on one side to the opposite side and to a flow channel arrangement arranged thereon in an alternating fashion, and then to be guided back to the first side from said opposite side and for said fluid to flow into a further downstream flow channel arrangement when viewed in the longitudinal direction of the flow limiter.

A surgical system according to the invention is designed, in particular, as an ophthalmological microsurgical system for lens surgery. The surgical system comprises an aspiration device with an aspiration branch having a flow limiter for a fluid flowing in the aspiration branch assigned thereto, the fluid being a surgical fluid with emulsified particles in the case of a surgical intervention. The flow limiter comprises at least one limiter element which comprises at least one flow channel arrangement with at least one main channel and one secondary channel which opens into the main channel at an angle of 90° or more. When suctioning off lens remains from the eye in particular, this design affords the possibility of substantially limiting the pressure pulse or the pressure oscillations resulting in the case of a breakthrough of a lens particle blocking the aspiration branch. This can very effectively prevent a relatively high volume from being suctioned out of the eye in the case of such a particle breakthrough.

In particular, the secondary channel opens into the main channel with both ends.

The surgical system is preferably designed such that a turbulent flow of the fluid can be generated in the flow limiter as a function of a specific operational state of the surgical system, particularly in the case of a breakthrough of a particle through a constriction in the aspiration device.

Advantageous refinements of the surgical system according to the invention are specified in the dependent claims.

Moreover, advantageous refinements of the flow limiter according to the invention should also be considered to be advantageous embodiments of the surgical system.

BRIEF DESCRIPTION OF THE DRAWINGS

Exemplary embodiments of the invention are explained in more detail below on the basis of schematic drawings, in which

FIG. 2a shows a plan view of a first exemplary embodiment of a flow limiter according to the invention;

FIG. 2b shows a perspective illustration of the flow limiter in accordance with FIG. 2a;

FIG. 3a shows a plan view of a second exemplary embodiment of a flow limiter according to the invention;

FIG. 3b shows a perspective illustration of a flow limiter in accordance with FIG. 3a;

FIG. 4a shows a perspective illustration of a third exemplary embodiment of a flow limiter according to the invention in accordance with a front view;

FIG. 4b shows a perspective illustration of the flow limiter in accordance with FIG. 4a in accordance with a rear view;

FIG. 5a shows a perspective illustration of a fourth exemplary embodiment of a flow limiter according to the invention in accordance with a front view;

FIG. 5b shows a further perspective illustration of the flow limiter in accordance with FIG. 5a in accordance with a rear view;

FIGS. 9a to 9p show schematic illustrations of different flow channel arrangements in a flow limiter.

PREFERRED EMBODIMENT OF THE INVENTION

In the figures, the same or functionally equivalent elements are provided with the same reference signs.

Figure 1:
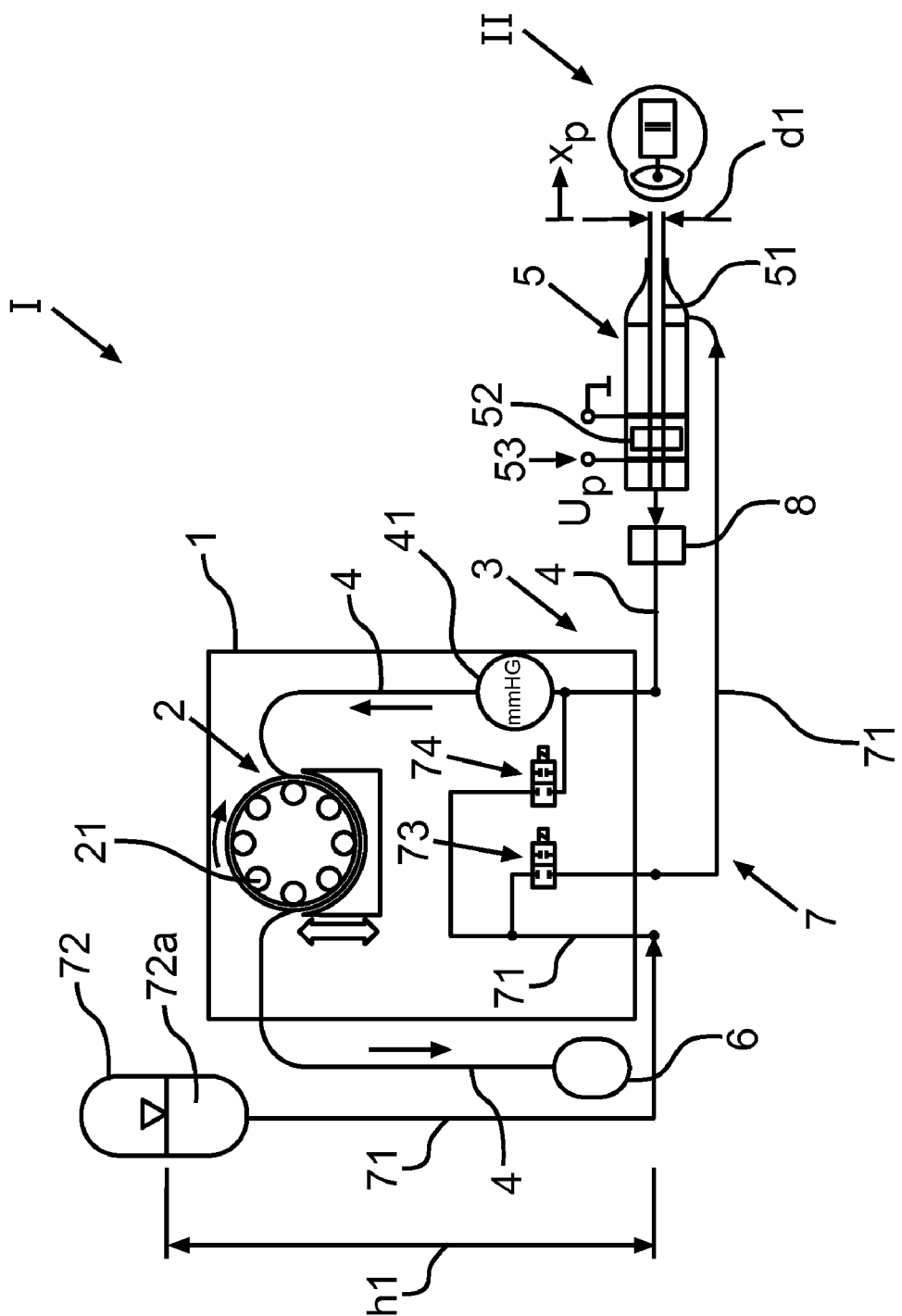
FIG. 1 shows a schematic illustration of a surgical system according to the invention.

FIG. 1 shows, in a schematic illustration, an ophthalmological microsurgical system I for lens surgery. Only the essential components of the system I which are required for understanding the invention are shown in the illustration in accordance with FIG. 1.

The surgical system I comprises an equipment unit 1 which can, for example, be designed as a trolley or the like and which also has a pump 2 in addition to electrical control units, driver units, a user interface and a display unit. In the exemplary embodiment, this pump 2 is designed as a peristaltic pump and hence as a pump which delivers in a discontinuous fashion in an active operational state. The pump 2 comprises a multiplicity of roller wheels 21 which are arranged at a distance from one another in the direction of the rotation (arrow) and which each remove a closed-off volume chamber from the suction region. The pump 2 is arranged in an aspiration branch 3 of the surgical system I and delivers the liquid which is contained in an aspiration line 4 of the aspiration branch 3, from a surgical handpiece 5, which is the phaco-handpiece in the exemplary embodiment, to a collection container 6. As a result of its design, the pump 2 is conceived such that the roller wheels 21 are designed so as not to contact the fluid flowing in the aspiration line 4 and so there is no direct connection between the roller wheels 21 and the fluid.

The handpiece 5 comprises a tip or a hollow needle 51 which is excited to oscillate by an ultrasound transducer 52. By way of example, the ultrasound transducer 52 can be piezoelectric and be excited to oscillate by an electrical voltage. The voltage is generated by a symbolically illustrated voltage source 53. An opening which has an internal diameter d1 as its internal dimension is provided on the front side of the hollow needle 51 which has a round cross section and faces the eye II. The diameter d1 is smaller than the diameter of the remainder of the hollow needle 51, as a result of which the hollow needle 51 has a tapered design at this front opening.

Moreover, the surgical system I comprises an irrigation branch 7 with an irrigation line 71 which extends between a container 72 with a rinsing fluid 72a and the handpiece 5. By way of example, the rinsing fluid 72a can be a saline. The illustration in FIG. 1 shows that the container 72 is at a height-level h1 compared to the handpiece 5, as a result of which the pressure of the rinsing fluid 72a in the irrigation line 71 can be varied as a function of this height h1. Furthermore, a valve 73 is arranged in the irrigation line 71. The irrigation line 71 is connected to the aspiration line 4 by a tube connection, with a further valve 74 being arranged in this tube connection.

Moreover, a pressure gauge 41 is arranged in the aspiration branch 3, which gauge is in the aspiration line 4 in the exemplary embodiment, downstream of the connection line to the irrigation line 71 in the flow direction of the fluid.

During the surgical procedure on the eye II, the rinsing fluid 72a supplied via the irrigation line 71 is suctioned off with the fragmented remains of the lens by the pump 2 via the hollow needle 51 and the aspiration line 4. The fluid suctioned off via the aspiration line 4 therefore is a surgical fluid which comprises emulsified particles in the case of a surgical intervention.

The surgical system I furthermore comprises a flow limiter 8 which is arranged in the aspiration branch 3, upstream of the pump 2 in the flow direction (arrow) of the fluid in the aspiration line 4; this flow limiter is provided exclusively for aspirative fluid transport.

The flow limiter 8 is not directly connected to the irrigation line 71.

In FIG. 1, the flow limiter 8 is merely illustrated by a symbolic block element and is arranged relatively close to the handpiece 5. A fluid is only transported through the flow limiter 8 in an aspirative fashion. The flow limiter is designed for flow rates of approximately 200 ml per minute. In the illustrated embodiment, the flow limiter 8 is arranged at a distance from both the handpiece 5 and the pump 2. Provision can also be made for the flow limiter 8 to at least in part be arranged in the handpiece 5 or to be arranged directly on the rear end of the handpiece 5 which opens into the aspiration line 4.

There can be blockages at the front tip of the hollow needle 51 as a result of the lens remains when said lens remains are suctioned out of the eye II. When this blocking lens particle then breaks through and is suctioned off through the aspiration system, the flow limiter 8 substantially limits or damps the shock wave in the flowing fluid generated by the breakthrough. This can prevent a critical surgical state in which a large volume can briefly be suctioned out of the eye as a result of this particle breakthrough and the unrestricted shock wave. This shock wave ("surge flow" or "surge pressure") is restricted by the flow limiter 8 such that this suctioning away from the eye and the reduction in the intraocular pressure connected therewith can be prevented.

In general terms, it is the object of hydraulic problems to determine the pressure loss of line elements through which fluid flows such as pipes, diaphragms, jets and the like. The pressure loss coefficient $\zeta$ detects the pressure losses. The pressure loss coefficient $\zeta$ is constant in the case of turbulent flow and the pressure loss is proportional to the square of the average speed $v_m$. The pressure loss can be determined from the following equation:

$$\Delta p = \zeta \cdot \frac{\rho}{2} \cdot v_m^2 = \zeta \cdot \frac{\rho}{2} \cdot \frac{Q^2 \cdot 16}{\pi^2 \cdot d^4} = \zeta \cdot \frac{\rho \cdot v^2}{2 \cdot d^2} \cdot Re^2,$$

where $\rho$ [kg/m³] describes the fluid density, Q [cc/min] describes the flow rate, d [mm] describes the diameter of the pipe or the like, $v$ [mm²/sec] describes the viscosity and Re describes the Reynolds number.

The Reynolds number Re is the characteristic of turbulent flows and can be specified as follows:

$$Re = \frac{d \cdot v_m}{v} = \frac{4 \cdot Q}{\pi \cdot d \cdot v}.$$

In the exemplary embodiment, the hollow needle 51 has a round cross section and the internal dimension of the hollow needle 51 then specified as the internal diameter d1 has a value of less than 1 mm, in particular approximately 0.9 mm, at the front tapered tip. Moreover, in the exemplary embodiment, the minimum internal dimension d2 (see FIG. 2a, for example) of the flow limiter 8 is significantly greater than this internal diameter d1. In the exemplary embodiment, the internal dimension d2 is approximately 1.2 mm. The fact that the internal dimension d2 is greater than, in particular significantly greater than, the minimum internal diameter d1 of the hollow needle 51 affords the possibility of also pulling the emulsion through the flow limiter 8 without any problems, said emulsion having previously been pulled through the narrow cross section of the hollow needle 51. Under these structural conditions, the flow limiter 8 is designed for the Reynolds range with Re less than 2000 so as to ensure an undisturbed surgical progress in respect of the suctioning off in the aspiration branch 3.

Furthermore, the entire flow limiter 8 is designed such that a turbulent flow can be generated in the flow limiter 8 when this particle breakthrough occurs and such that, in the case of the mentioned Reynolds numbers Re of less than 2000, in its entirety it has a resistance of at least 500 mmHg and a pressure loss coefficient $\zeta$ of 85 in the exemplary embodiment.

The basic design of the flow limiter 8 is designed such that a flow resistance element based on the effect of counter-flowing flow profiles is present. The greatest amount of turbulence in the flow limiter 8 occurs in the mixing area of the coincident flows.

Different exemplary embodiments of a flow limiter 8 will be described in more detail in the following text.

Figures 2A, 2B:
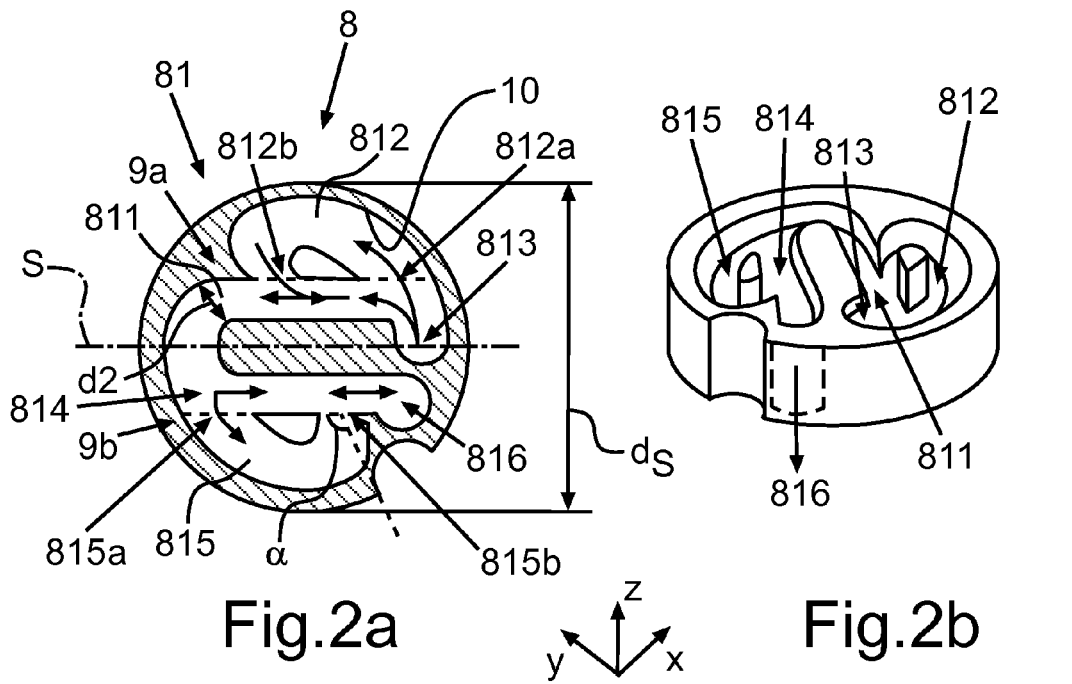

FIG. 2a shows a limiter element 81 of a flow limiter with a disk-like design. In the illustrated embodiment, a flow limiter 8 can have at least one such limiter element 81. Provision can also be made for a plurality of such limiter elements 81 to be provided, which limiter elements are then arranged directly adjoining one another and are stacked in the z-direction. The at least two limiter elements 81 can then be interconnected in a nondestructive detachable fashion and hence be reversibly detachable and recombinable.

The limiter element 81 has an external diameter $d_S$ which is less than or equal to the diameter of the handpiece 5.

In the plan view illustration in accordance with FIG. 2a, the limiter element 81 has a first flow channel arrangement 9a comprising a main channel 811 and a secondary channel 812. In the flow direction (arrows) of the fluid, the first end of the secondary channel 812 branches off at an inlet 812a and its second end opens back into the main channel 811 at a confluence 812b. The fluid suctioned off by the handpiece 5, and by the aspiration branch of the handpiece 5 in particular, which comprises the lens particles enters the limiter element 81 at an inlet 813 and then flows in the direction of the illustrated arrows. In the embodiment in accordance with FIG. 2a, the main channel 811 has a substantially straight-lined profile between the branch-off and confluence locations of the secondary channel 812. The secondary channel 812 is designed like a loop and particularly the end which opens into the main channel 811 at the confluence 812b is bent or designed such that the flow of the fluid entering the main channel 811 from the secondary channel 812 enters in the direction of the inlet 813. Hence, the flows of the fluid in the secondary channel 812 and in the main channel 811 generate counter-flowing flow profiles at an angle of greater than 90° in the confluence 812b.

If there is a particle breakthrough at the front opening of the hollow needle 51, a large flow resistance is generated particularly in this region of the confluence 812b as a result of forming turbulent flow. Hence, the occurrence of a shock wave as a result of the particle breakthrough can be prevented and as a result of this it is also possible to prevent the brief suctioning off of high volumes from the eye II when such a particle breakthrough occurs.

In the illustrated embodiment in accordance with FIG. 2a, the limiter element 81 comprises a second flow channel arrangement 9b which likewise comprises a main channel 814 and a secondary channel 815. A first end of the secondary channel 815 branches off at the branch-off 815a and the second end of said channel opens back into the main channel 814 at the confluence 815b. The shape and arrangement of the second secondary channel 815 with respect to the second main channel 814 is analogous to the design of the main channel 811 and secondary channel 812 of the first flow channel arrangement 9a. The fluid flowing in the limiter element 81 is then emitted at the outlet 816 and is delivered to the container 6 via the aspiration line 4 and the pump 2.

The second flow channel arrangement 9b is arranged in series with the first flow channel arrangement 9a. The two flow channel arrangements 9a and 9b of the limiter element 81 have a mirror-symmetrical design in respect of the axis S.

The internal diameter d2 of the region of the limiter element 81 through which fluid flows and hence, in particular, the flow channel arrangements 9a and 9b with their respectively assigned channels remain substantially unchanged over the entire length.

Provision can preferably also be made for this in the further embodiments of the flow limiter 8 which still need to be explained.

However, in principle, the minimum internal diameter d2 of the region of a flow limiter 8 through which fluid flows can change over the length thereof.

In the illustrated embodiment in accordance with FIG. 2a, the inner walls 10 which delimit the region of the limiter element 81 through which fluid flows are designed to be stiff. This means that force actions, as are generated on these inner walls 10 by the flowing fluid and by pressure pulsations of the flowing fluid in particular, do not lead to an elastic deformation of these inner walls 10.

However, provision can also be made for a flow limiter 8 at least in part having inner walls 10 which have an elastic design in respect of such force actions of a flowing fluid in the case of pressure pulsations.

The main channels 811 and 814 and the respectively associated secondary channels 812 and 815 are arranged such that they have an angle α of greater than 90° at the confluences 812*b* and 815*b* (said angle is only illustrated in the second flow channel arrangement 9*b* for reasons of clarity). Moreover, in the exemplary embodiment, the channels of the flow limiter 81 are dimensioned such that they have the same hydraulic diameter. Hence, it is also possible for a main channel 811 or 814 and a respective secondary channel 812 or 815 to have different cross sectional geometries but to have such dimensions that the resistance acting on the fluid is of the same magnitude.

FIG. 2*b* shows a perspective illustration of the disk-shaped limiter element 81.

The main channels 811 and 814 and the secondary channels 812 and 815 extend in a plane (x-y plane) which is arranged perpendicularly with respect to the extent (z-direction) of the outlet 816 and the inlet 813.

Figures 3A, 3B:
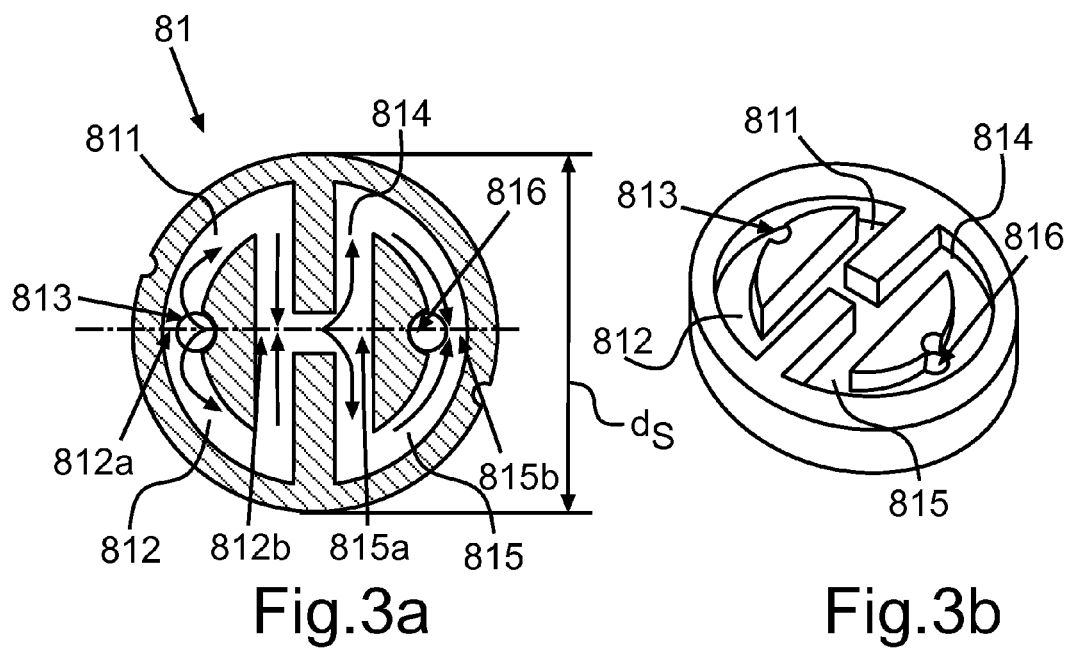

FIG. 3*a* illustrates a plan view of a further exemplary embodiment of a limiter element 81. In this embodiment, the main channel 811 and the secondary channel 812 of the first flow channel arrangement 9*a* have virtually the same design. Both channels 811 and 812 respectively have an arc-shaped portion which then respectively merges into a straight-lined channel section in an angled fashion. The main channel 811 and the secondary channel 812 are formed substantially symmetrically in respect of a horizontal axis extending through the inlet 813 and the outlet 816. The straight-lined portions of the channels 811 and 812 are oriented and aligned with respect to one another such that the flow profiles of the flowing fluid are aligned directly toward each other.

The channels 814 and 815 of the second flow channel arrangement 9*b* of the limiter element 81 are arranged in a corresponding fashion. Unlike the arrangement of the channels 811 and 812, when viewed in the flow direction, the channels 814 and 815 respectively firstly have a straight-lined channel section which then merges into a respective arc-shaped portion in an angled fashion. The arc-shaped portions of the main channel 814 and the secondary channel 815 then open back into one another at the confluence 815*b* such that the flow profiles substantially run toward one another from opposing directions.

FIG. 3*b* shows a perspective illustration of the limiter element 81 in accordance with FIG. 3*a*. Here, it can also be seen in turn that the channels 811, 812, 814 and 815 are formed in a plane which extends perpendicularly with respect to the orientation of the inlet 813 and the outlet 816. Every limiter element 81 with a main and a secondary channel is preferably designed such that it has a pressure loss coefficient ζ per limiter element 81 which is greater than or equal to 6, in particular greater than or equal to 12. In particular, taking into account the predetermined internal dimensions d1 and d2 and a Reynolds number Re of less than 2000, such a design of a limiter element 81, and hence of a flow limiter 8 as well, can prevent a very effective limitation or reduction of a pressure pulse (surge flow) or a tension pulse when there is a breakthrough of a particle. A flow limiter 8 preferably comprises so many limiter elements 81 that in total a pressure loss coefficient ζ equaling 85 is obtained.

In the exemplary embodiments illustrated in FIGS. 2*a*, 2*b*, 3*a* and 3*b*, the flow channel arrangements 9*a* and 9*b* extend in a plane (x-y plane). The limiter element 81 is preferably arranged in the aspiration line 4 such that this plane is oriented perpendicularly with respect to the longitudinal direction (z-direction) of the aspiration line 4. This direction (z-direction) also corresponds to the direction of the inlet 813 and the outlet 816.

FIG. 4*a* illustrates a further exemplary embodiment of a flow limiter 8. In this embodiment, the flow limiter 8 is of a rod-shaped design and comprises a rod-shaped internal part 8*a* and an external part 8*b*. A nozzle-shaped connector 8*c* is formed on the internal part 8*a*, which nozzle affords a connection to the handpiece 5 or to the aspiration line 4 which is within the handpiece or outside of the handpiece 5. Moreover, the connector 8*d* on the external part 8*b* on the side facing the pump 2 affords a connection with the aspiration line 4.

In the illustrated embodiment, the internal part 8*a* has a plurality of flow channel arrangements in the longitudinal direction (x-direction), and hence in the longitudinal direction A of the flow limiter 8 as well. The flow channel arrangements are designed in accordance with the refinement of FIGS. 2*a* and 2*b*.

Hence, the internal part 8*a* comprises a multiplicity of flow channel arrangements arranged in a cascading fashion. Three flow channel arrangements, each with a main channel 811 and a secondary channel 812, are identified in more detail on the front side of the internal part 8*a* shown in FIG. 4*a*. Corresponding flow channel arrangements are formed in a corresponding fashion on the opposing rear side of the internal part 8*a*; this is illustrated in FIG. 4*b*. Hence, the fluid with the lens remains to be suctioned off over the aspiration branch 3 flows into the flow limiter 8 via the connector 8*c* and then, for example, in further progression flows into the channels 811 and 812 via first inlet 813 of the limiter element 81*a* and emerges at the outlet 816. This outlet 816 is connected to an opposing limiter element 81*e*, and there the fluid flows into the corresponding channels 811 and 812 via the inlet 813 illustrated in FIG. 4*b*. Hence, the limiter elements 81*a*, 81*b* and 81*c* (FIG. 4*a*) are alternately connected in series to a limiter element 81*d*, 81*e*, 81*f* arranged on the opposite side (FIG. 4*b*) of the internal part 8*a*. The latter elements have analogous designs to the limiter elements 81*a* to 81*c* and likewise each have a main channel 814 and a secondary channel 815.

The illustrations in FIGS. 4*a* and 4*b* show that the flow channel arrangements are formed on the shell of the internal part 8*a* and hence have a design which is virtually open toward the outside. In order to close-off or cover these open flow channels, the internal part 8*a* is inserted into the hollow external part 8*b* in an accurately fitting fashion. An inner side or an inner wall of the external part 8*b* thus forms a tight cover for the open flow channel arrangements in the internal part 8*a*. This design of a flow limiter 8 makes it possible to develop a detachable connection between the elements, which connection constitutes a simple coupling or plug connection.

In the illustrated embodiment in accordance with FIGS. 4*a* and 4*b*, the main channels 811 and 814 are oriented in a fashion which is substantially perpendicular to the axis A.

FIG. 5*a* shows a perspective illustration of a further exemplary embodiment of a flow limiter 8. A principle which corresponds to the embodiment of FIGS. 4*a* and 4*b* is also realized in this case. In contrast thereto, the internal part 8*a* in the embodiment in accordance with FIG. 5*a* has a cylindrical shape and has a round base. In the embodiment in accordance with FIG. 4a, the base of the internal part is oval or rectangular with rounded short sides. Moreover, the embodiment in FIG. 5a differs in that the main channels 811 are basically oriented parallel to the axis A. The shape and arrangement between a main channel 811 and 814 and a secondary channel 812 and 815 in turn corresponds to the refinement in accordance with FIG. 2a or FIG. 4a. Moreover, the flow channel arrangements are basically arranged adjacent to one another and are only separated by a separating wall 817.

FIG. 5b shows a further perspective illustration of this embodiment of the flow limiter 8.

Figure 6:
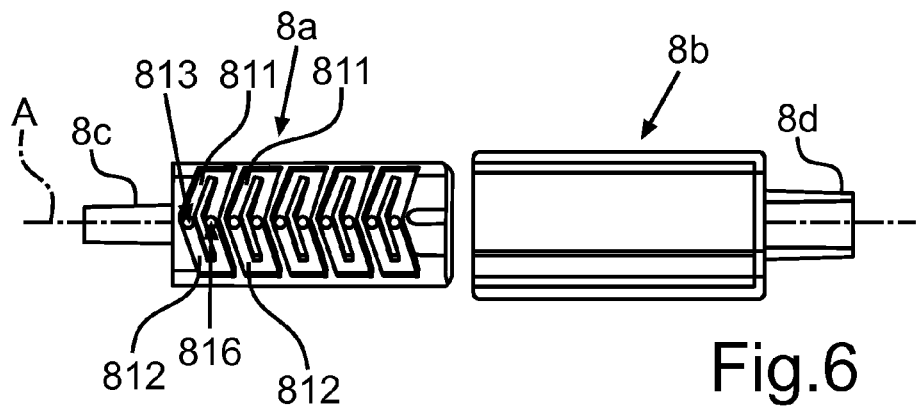
FIG. 6 shows a perspective illustration of a fifth exemplary embodiment of a flow limiter according to the invention.

FIG. 6 shows a further exemplary embodiment of a flow limiter 8 in a perspective view. Here too, a principle is realized in which a rod-shaped internal part 8a is designed as a part which is separate to an external part 8b. In this embodiment, the main channels 811 and the secondary channels 812 are arranged virtually symmetrically with respect to the longitudinal axis A and have a design tilting away from the connector 8c.

Figure 7:
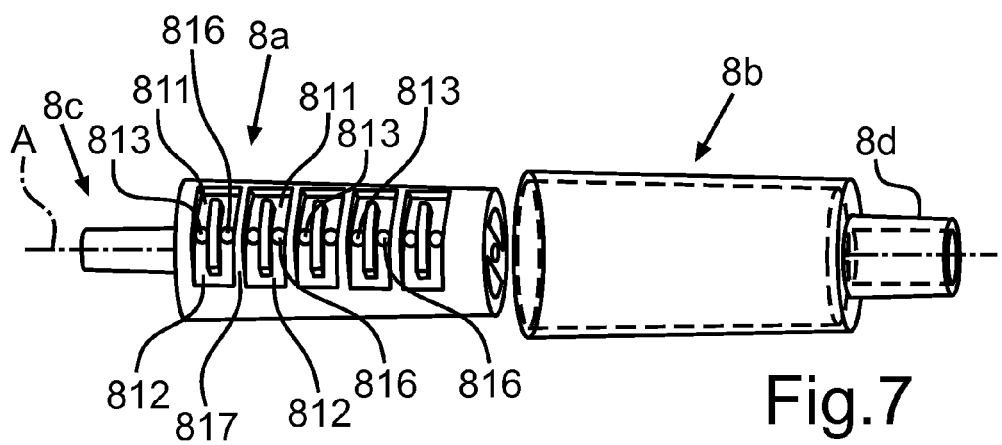
FIG. 7 shows a perspective illustration of a sixth exemplary embodiment of a flow limiter according to the invention.

FIG. 7 shows a further embodiment of a flow limiter 8 in which, unlike the refinement in accordance with FIG. 6, the main channels 811 and secondary channels 812 arranged symmetrically with respect to one another do not have an away tilt in respect of the connector 8c.

Figure 8:
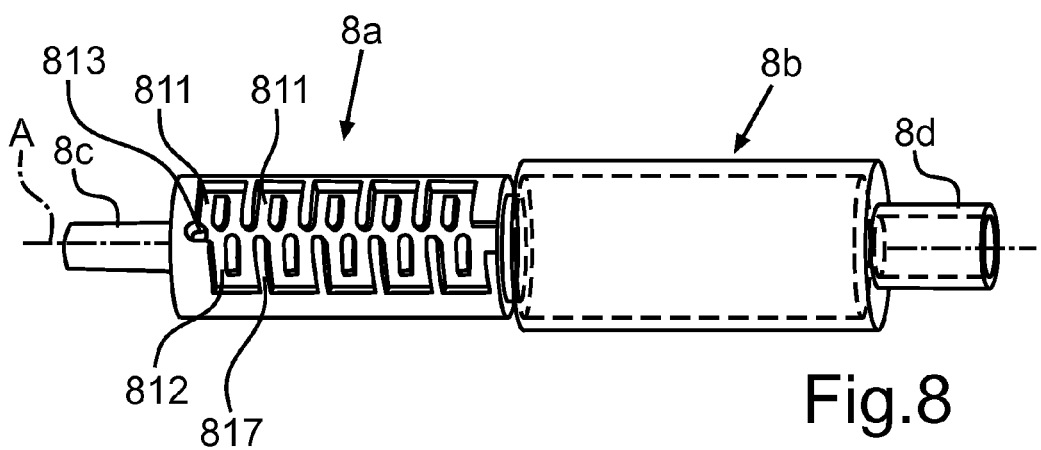
FIG. 8 shows a perspective illustration of a seventh exemplary embodiment of a flow limiter according to the invention.

FIG. 8 shows a further embodiment in a perspective illustration, in which a flow limiter 8 in turn comprises an internal part 8a and an external part 8b. In contrast to the embodiment in accordance with FIG. 7, the main channels 811 guided in a U-shape and the secondary channels 812 guided in a U-shaped are arranged offset with respect to one another along the longitudinal axis A. Moreover, the limiter elements arranged in series are no longer completely separate from one another but there are cuts through the separating walls 817. Moreover, there is only an inlet 813 at the start.

In the embodiments in FIGS. 4a to 8, the flow channel arrangements are no longer merely arranged in a plane but extend in stepped fashion as a three-dimensional shape. When viewed in the longitudinal direction and hence in the direction of the axis A, flow channel arrangements which are connected in a flow-technical fashion are in each case arranged at the same height on both sides of the axis A.

Figures 9I, 9J, 9K, 9L, 9M, 9N, 9O, 9P:
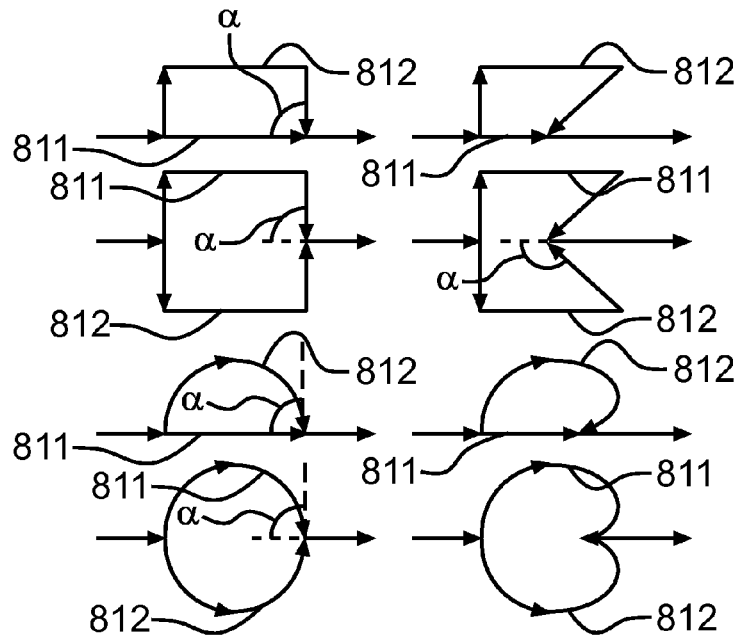

FIGS. 9a to 9p show a plurality of different schematic refinements of flow channel arrangements 9a and 9b. Thus, provision can be made for a secondary channel 812 to have an angled channel profile or have an at least in part angled channel profile. Likewise, provision can be made for a channel profile which is at least in part bent. The branch-off of a secondary channel 812 from a main channel 811 can be effected at an angle of 90°. However, provision can likewise be made for the branch-off to also have an angle of less than 90° or greater than 90°.

The confluence of the secondary channel 812 into the main channel 811 is effected at an angle α of 90° or at an angle greater than 90°. As is shown, for example, in FIGS. 9a to 9d, the secondary channels 812 can branch off from the main channel 811, alternately toward the top and then toward the bottom, in a series connection of the flow channel arrangements 9a and 9b. A corresponding refinement is shown in FIGS. 9m to 9p. FIGS. 9e to 9l show embodiments in which respectively two different illustrations of a single flow channel arrangement are shown. By way of example, symmetric embodiments in respect of a horizontal axis of symmetry can also be provided here.

Some embodiments in FIGS. 9a to 9p show, in an exemplary fashion, the angles α between a main channel and a secondary channel; these are all at an angle of 90° or more.

The embodiments illustrated in FIGS. 2a to 9p can, in part or overall, be combined with one another in an arbitrary fashion in order to be able to obtain additional embodiments of a flow limiter.

Figure 10:
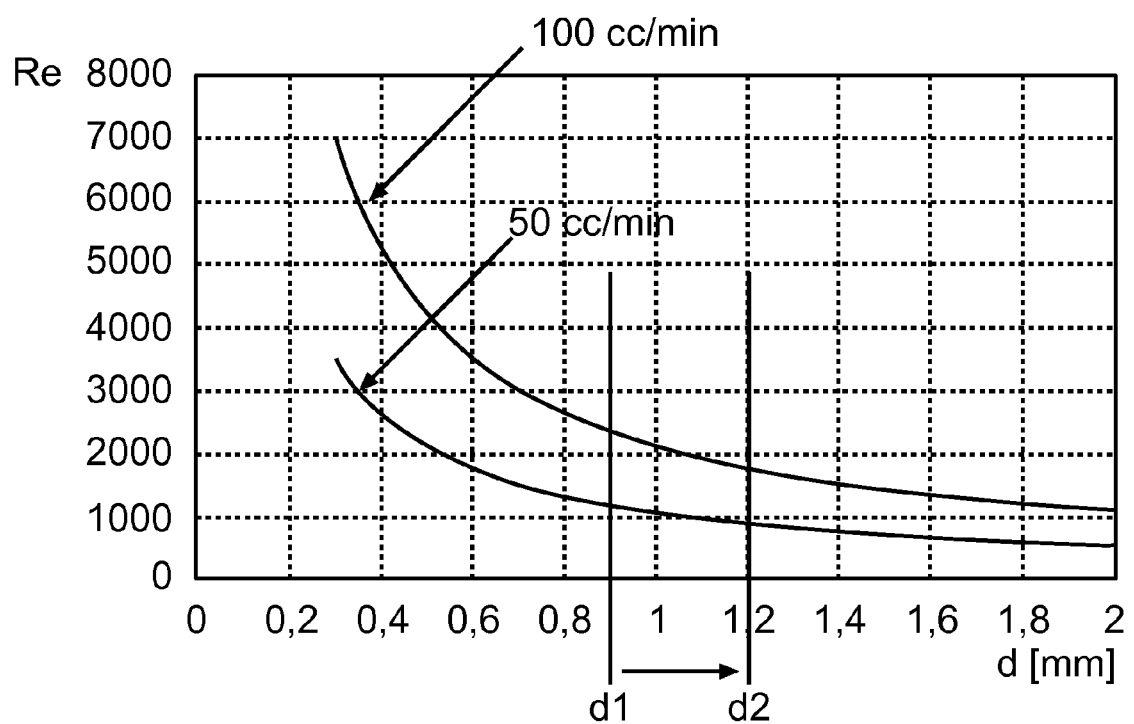
FIG. 10 shows a diagram in which the Reynolds number is plotted as a function of an internal dimension of a line.

FIG. 10 shows a diagram which plots the Reynolds number Re as a function of an internal dimension d. Shown here are the internal diameter d1 of the hollow needle 51 and the internal dimension d2 of a flow channel of the flow limiter 8.

The invention claimed is:

1. A flow limiter, comprising:
a limiter element comprising a flow channel arrangement comprising a main channel and a secondary channel, the secondary channel being outside the main channel, the secondary channel having two ends which open into the main channel, at least one of the two ends of the secondary channel opening into the main channel at an angle of 90° or more,
wherein the flow limiter is configured to limit fluid flow in an aspiration branch of a surgical system.

2. The flow limiter as claimed in claim 1, wherein a turbulent flow can be generated in the flow limiter at a Reynolds number of less than 2000.

3. The flow limiter as claimed in claim 1, wherein a pressure loss coefficient ζ per limiter element of the flow limiter is greater than or equal to 6.

4. The flow limiter as claimed in claim 1, wherein a pressure loss coefficient ζ of the flow limiter has a value of 85.

5. The flow limiter as claimed in claim 1, wherein the secondary channel is arranged outside of the main channel, and a turbulent flow can be generated in a flow direction of the fluid at a confluence of the secondary channel into the main channel.

6. The flow limiter as claimed in claim 1, wherein the flow limiter has a region through which fluid flows with a minimum internal dimension greater than a minimum internal dimension of a hollow needle of a surgical handpiece which can be connected to the flow limiter in the aspiration branch.

7. The flow limiter as claimed in claim 6, wherein the minimum internal dimension of the region through which fluid flows is at least 10% greater than the minimum internal dimension of the hollow needle.

8. The flow limiter as claimed in claim 6, wherein the minimum internal dimension of the region through which fluid flows remains substantially unchanged over an entire length of the region through which fluid flows.

9. The flow limiter as claimed in claim 6, wherein the minimum internal dimension of the region through which fluid flows is greater than or equal to 1.2 mm.

10. The flow limiter as claimed in claim 1, wherein the fluid limiter is designed to have a flow rate greater than 190 ml per minute.

11. The flow limiter as claimed in claim 1, wherein the main channel and the secondary channel have the same hydraulic diameter.

12. The flow limiter as claimed in claim 1, comprising at least two limiter elements detachably connected to one another, wherein the two detachably connected limiter elements are in a stacked arrangement when viewed in a longitudinal direction of the flow limiter.

13. The flow limiter as claimed in claim 1, wherein the surgical system is an ophthalmological microsurgical system for lens surgery.

14. A surgical system, comprising:
an aspiration branch; and
a flow limiter in the aspiration branch to limit fluid flow in the aspiration branch, the flow limiter comprising a limiter element comprising a flow channel arrangement comprising a main channel and a secondary channel, the secondary channel being outside the main channel, the secondary channel having two ends which open into the main channel, at least one of the two ends of the secondary channel opening into the main channel at an angle of 90° or more with an aspiration branch having a flow limiter.

15. The surgical system as claimed in claim 14, further comprising a handpiece, wherein the flow limiter is arranged on the handpiece or at least partially arranged in the handpiece.

16. The surgical system as claimed in claim 14, wherein the surgical system is an ophthalmological microsurgical system for lens surgery.

17. The surgical system as claimed in claim 14, further comprising a handpiece comprising a hollow needle connected to the flow limiter in the aspiration branch, wherein the flow limiter has a region through which fluid flows with a minimum internal dimension greater than a minimum internal dimension of the hollow needle.

18. A method, comprising:
flowing a surgical fluid through a flow limiter located in an aspiration branch of a surgical system,
wherein the flow limiter comprises a limiter element comprising a channel arrangement comprising a main channel and a secondary channel, the secondary channel being outside the main channel, the secondary channel having two ends which open into the main channel, at least one of the two ends of the secondary channel opening which opens into the main channel at an angle of 90° or more.

19. The method as claimed in claim 18, wherein the surgical system is an ophthalmological microsurgical system for lens surgery.

20. The method as claimed in claim 18, wherein the surgical fluid comprises emulsified particles.

* * * * *

UNITED STATES PATENT AND TRADEMARK OFFICE
CERTIFICATE OF CORRECTION

| | |
|---|---|
| PATENT NO. | : 8,303,553 B2 |
| APPLICATION NO. | : 12/666059 |
| DATED | : November 6, 2012 |
| INVENTOR(S) | : Christoph Kuebler et al. |

It is certified that error appears in the above-identified patent and that said Letters Patent is hereby corrected as shown below:

Column 9, Line 48-50, delete "Reynolds range with...aspiration branch 3." insert same at
Column 9, line 47, after "the" as the continuation of same paragraph.

Column 9, Line 64, delete "with" insert --8 with--.

Column 12, Line 17, delete "or" insert --5 or--.

Column 16, Line 10, Claim 18, before "into" delete "which opens".

Signed and Sealed this
Nineteenth Day of February, 2013

Teresa Stanek Rea
*Acting Director of the United States Patent and Trademark Office*